(12) United States Patent
Nakayama et al.

(10) Patent No.: US 12,007,340 B2
(45) Date of Patent: Jun. 11, 2024

(54) X-RAY CT APPARATUS

(71) Applicant: SHIMADZU Techno-Research, Inc., Kyoto (JP)

(72) Inventors: Takashi Nakayama, Kyoto (JP); Atsuhiro Hayashi, Kyoto (JP)

(73) Assignee: SHIMADZU Techno-Research, Inc., Kyoto (JP)

( * ) Notice: Subject to any disclaimer, the term of this patent is extended or adjusted under 35 U.S.C. 154(b) by 287 days.

(21) Appl. No.: 17/624,554

(22) PCT Filed: Apr. 8, 2020

(86) PCT No.: PCT/JP2020/015783
§ 371 (c)(1),
(2) Date: Jan. 3, 2022

(87) PCT Pub. No.: WO2021/014696
PCT Pub. Date: Jan. 28, 2021

(65) Prior Publication Data
US 2022/0252528 A1  Aug. 11, 2022

(30) Foreign Application Priority Data
Jul. 25, 2019 (JP) .................................. 2019-136652

(51) Int. Cl.
*G01N 23/046* (2018.01)
*A61B 6/00* (2006.01)
*G01N 3/20* (2006.01)

(52) U.S. Cl.
CPC ............. *G01N 23/046* (2013.01); *A61B 6/54* (2013.01); *G01N 3/20* (2013.01)

(58) Field of Classification Search
CPC ........... G01N 23/046; G01N 3/20; A61B 6/54
See application file for complete search history.

(56) References Cited

U.S. PATENT DOCUMENTS 9,791,385 B2 * 10/2017 Mertens ............... G01N 23/046
2003/0035576 A1 * 2/2003 Roder ................... G06T 7/0004
382/145

(Continued)

FOREIGN PATENT DOCUMENTS

JP    2000298106    10/2000
JP    2004132931    4/2004

(Continued)

OTHER PUBLICATIONS

"Office Action of Japan Counterpart Application", issued on Oct. 18, 2022, with English translation thereof, pp. 1-6.

(Continued)

*Primary Examiner* — Hugh Maupin
(74) *Attorney, Agent, or Firm* — JCIPRNET

(57) ABSTRACT

The present invention provides an X-ray CT apparatus capable of obtaining a high-quality X-ray CT image by suppressing occurrence of an artifact. The X-ray CT apparatus including an X-ray imaging system including an X-ray irradiation unit and an X-ray detector, a rotating stage disposed between the X-ray irradiation unit and the X-ray detector, a rotation mechanism configured to relatively rotate the X-ray imaging system and the rotating stage about a rotation axis orthogonal to an optical axis of an X-ray that runs from the X-ray irradiation unit to the X-ray detector, and a load mechanism which is set on the stage and applies test force to a test piece includes an angle changing mechanism that tilts a bending tester to change the direction of the test force applied to the test piece by the bending tester from a direction orthogonal to the optical axis of the X-ray.

3 Claims, 10 Drawing Sheets

(56) References Cited

U.S. PATENT DOCUMENTS

| | | | | |
|---|---|---|---|---|
| 2010/0259910 | A1* | 10/2010 | Hayashi | B32B 15/14 |
| | | | | 361/783 |
| 2014/0064445 | A1* | 3/2014 | Adler | G01N 23/083 |
| | | | | 378/43 |
| 2019/0265139 | A1* | 8/2019 | Bodnyk | G01N 3/08 |
| 2020/0363344 | A1* | 11/2020 | Heo | G01N 23/046 |

FOREIGN PATENT DOCUMENTS

| | | |
|---|---|---|
| JP | 2006038836 | 2/2006 |
| JP | 2006214841 | 8/2006 |
| JP | 4059197 | 3/2008 |
| JP | 2008058227 | 3/2008 |
| JP | 2008249668 | 10/2008 |
| JP | 2013067409 | 4/2013 |
| JP | 2017032325 | 2/2017 |

OTHER PUBLICATIONS

"Office Action of Japan Counterpart Application", issued on May 30, 2023, with English translation thereof, pp. 1-4.

"International Search Report (Form PCT/ISA/210) of PCT/JP2020/015783," mailed on Jul. 14, 2020, with English translation thereof, pp. 1-6.

"Written Opinion of the International Searching Authority (Form PCT/ISA/237) of PCT/JP2020/015783," mailed on Jul. 14, 2020, with English translation thereof, pp. 1-5.

"Reconsideration Report by Examiner before Appeal of Japan Counterpart Application", with English translation thereof, issued on Oct. 5, 2023, p. 1-p. 6.

"Office Action of China Counterpart Application", issued on Jan. 19, 2024, with English translation thereof, p. 1-p. 15.

* cited by examiner

X-RAY CT APPARATUS

CROSS-REFERENCE TO RELATED APPLICATION

This application is a 371 application of the International PCT application serial no. PCT/JP2020/015783, filed on Apr. 8, 2020, which claims the priority benefits of Japan Patent Application No. 2019-136652, filed on Jul. 25, 2019. The entirety of each of the above-mentioned patent applications is hereby incorporated by reference herein and made a part of this specification.

TECHNICAL FIELD

The present invention relates to an X-ray CT apparatus.

BACKGROUND ART

In a material test in which test force is applied to a test piece to examine characteristics of a material, such as strength, X-ray CT imaging may be performed on the test piece to which the test force is applied in order to observe a state of internal fracture in the test piece. An industrial X-ray CT apparatus includes an X-ray irradiation unit, an X-ray detector disposed opposite to the X-ray irradiation unit, and a stage disposed between the X-ray irradiation unit and the X-ray detector for rotating a test piece placed on it. The X-ray CT apparatus is configured to observe a three-dimensional internal structure of the test piece by executing X-ray fluoroscopy while rotating the stage. A type of CT imaging apparatus that performs X-ray CT imaging of a test piece while test force is applied to the test piece is also used (see Patent Literature 1).

CITATION LIST

Patent Literature

Patent Literature 1: JP 4059197 B2

SUMMARY OF INVENTION

Technical Problem

FIG. 10 is a schematic view illustrating a bending test performed on a printed circuit board as a test piece in a CT imaging apparatus which performs X-ray CT imaging while test force is applied to the test piece.

The printed circuit board includes a board 102, and an electronic component 101 joined to the board 102 by solder joints 103. Test force is applied downward to apply a bending stress to the printed circuit board as a test piece, as indicated by an arrow 107, and the printed circuit board is rotated about a vertical rotation axis 100. In this state, X-ray CT imaging is performed on the printed circuit board by an X-ray detector 105 detecting an X-ray that is emitted from an X-ray irradiation unit 104 and has passed through the printed circuit board.

In the X-ray CT imaging performed with such a configuration, a plurality of solder joints 103 in the observation target region revolve in a plane, and metal contained in the solder joints 103 causes a metal artifact in an image captured by the X-ray detector 105. Occurrence of such a noticeable artifact makes it difficult to accurately observe the observation target region including the solder joints 103.

This problem occurs not only in a case where a printed circuit board is used as a test piece but also in X-ray CT imaging performed on a test piece of carbon fiber reinforced plastic (CFRP) or glass fiber reinforced plastic (GFRP) with an X-ray passing through a large distance in the test piece.

The present invention has been made to solve the above-mentioned problem. An object of the present invention is to provide an X-ray CT apparatus capable of obtaining a high-quality X-ray CT image by suppressing the occurrence of an artifact.

Solution to Problem

A first aspect of the present invention is an X-ray CT apparatus including an X-ray imaging system including an X-ray irradiation unit and an X-ray detector, a stage disposed between the X-ray irradiation unit and the X-ray detector, a rotation mechanism configured to relatively rotate the X-ray imaging system and the stage about a rotation axis orthogonal to an optical axis of an X-ray that runs from the X-ray irradiation unit to the X-ray detector, and a load mechanism which is set on the stage and is configured to apply test force to a test piece, the X-ray CT apparatus including an angle changing mechanism configured to tilt the load mechanism to change a direction of the test force applied to the test piece by the load mechanism from a direction orthogonal to the optical axis of the X-ray.

Advantageous Effects of Invention

According to a first aspect of the present invention, a load mechanism is tilted to change the direction of the test force applied to a test piece by the load mechanism from a direction orthogonal to the optical axis of an X-ray, and thereby the occurrence of an artifact is suppressed and a high-quality X-ray CT image can be obtained.

DESCRIPTION OF EMBODIMENTS

Figure 1:
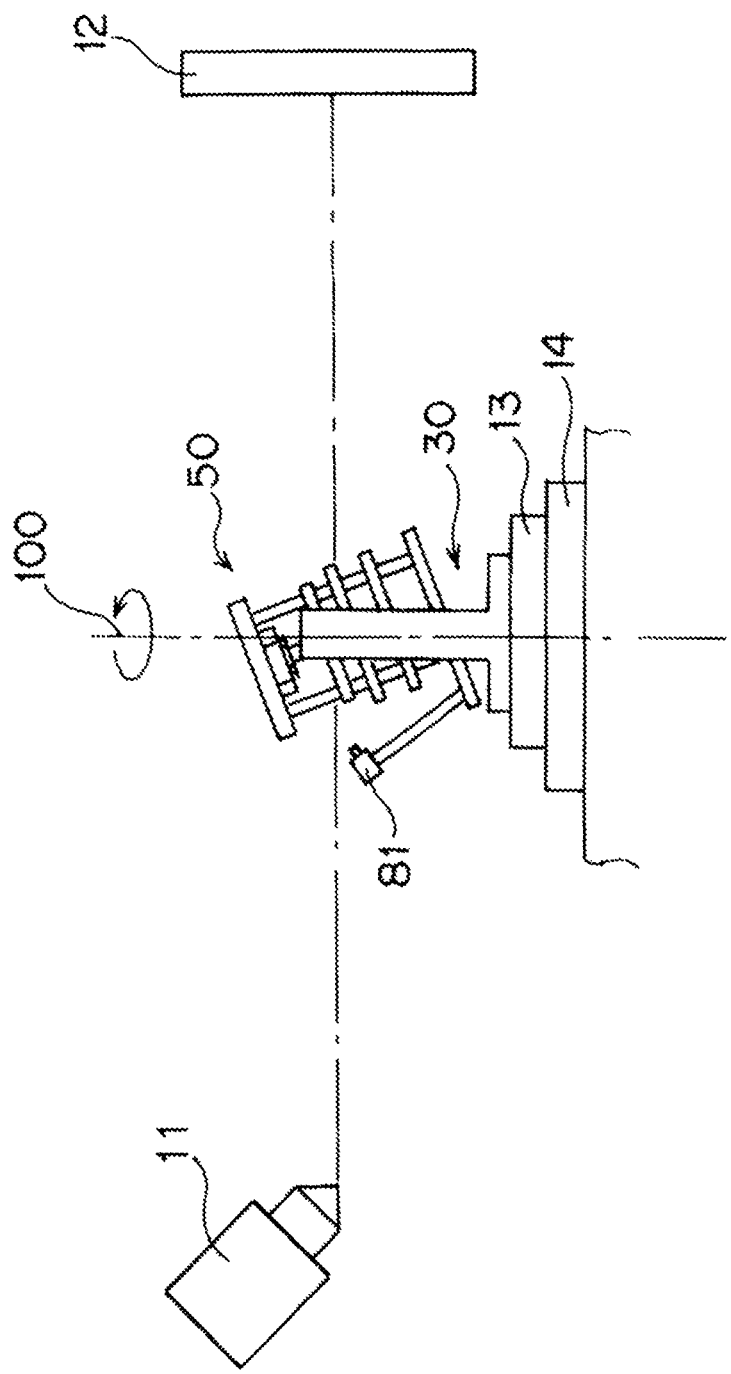
FIG. 1 is a schematic view of an X-ray CT apparatus according to an embodiment of the present invention.
Figure 2:
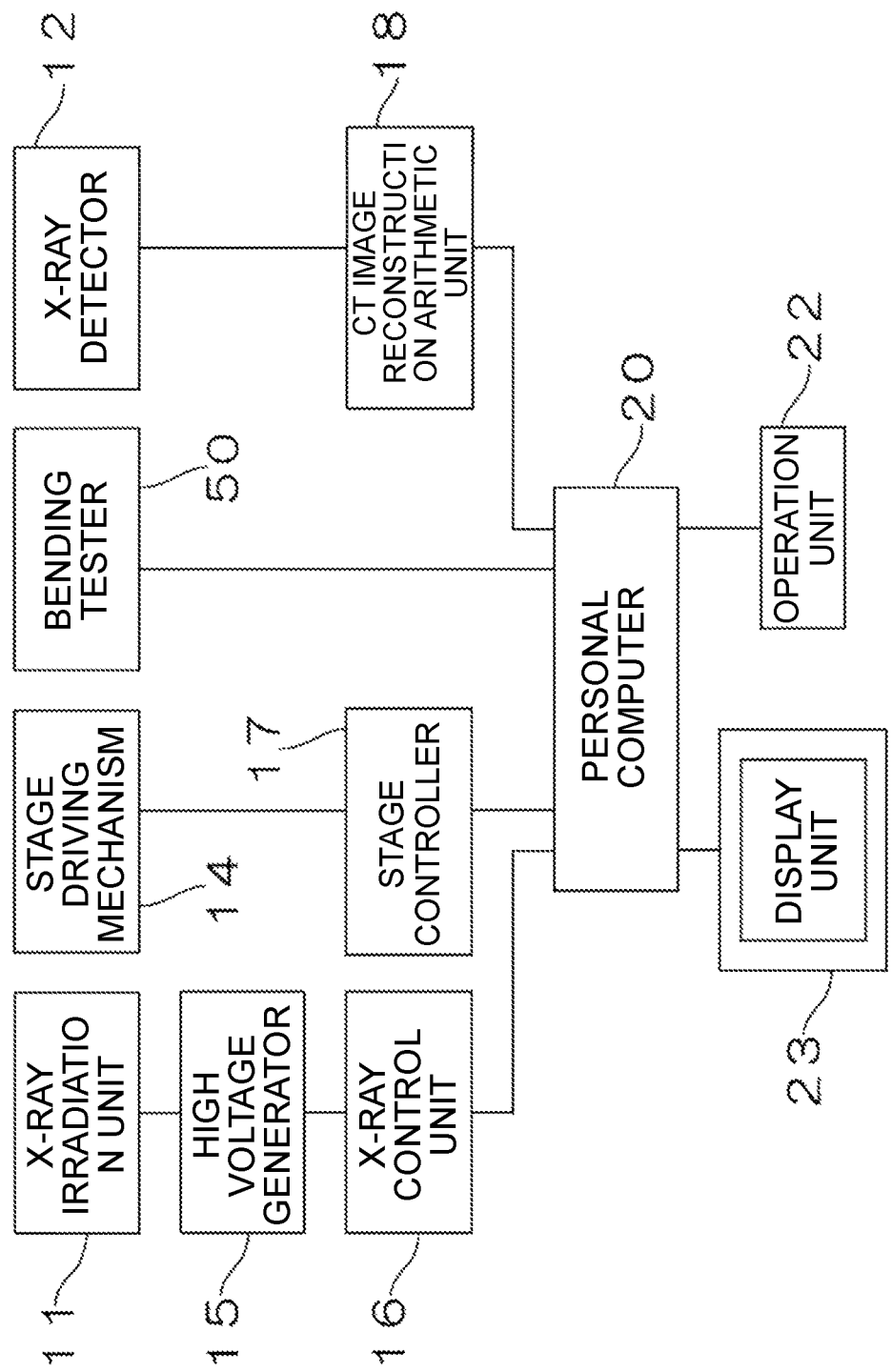
FIG. 2 is a block diagram illustrating a main control system of the X-ray CT apparatus according to the embodiment of the present invention.

Hereinafter, an embodiment of the present invention will be described with reference to the drawings. FIG. 1 is a schematic view of an X-ray CT apparatus according to an embodiment of the present invention. FIG. 2 is a block diagram illustrating a main control system of the X-ray CT apparatus according to the embodiment of the present invention.

The X-ray CT apparatus includes an X-ray irradiation unit 11, an X-ray detector 12, and a rotating stage 13. This X-ray CT apparatus performs non-destructive internal observation on a test piece TP by X-ray CT imaging. In the X-ray CT apparatus, a bending tester 50 as a load mechanism according to the present invention is set on the rotating stage 13 disposed between the X-ray irradiation unit 11 and the X-ray detector 12 disposed opposite to each other, the test piece TP is rotated together with the bending tester 50, and a load is applied to the test piece TP by the bending tester 50. The bending tester 50 is set on the rotating stage 13 via an angle changing mechanism 30 described later.

The X-ray irradiation unit 11 includes inside an X-ray tube as an X-ray source, and generates from the X-ray tube an X-ray corresponding to a tube voltage and a tube current supplied from a high voltage generator 15. The high voltage generator 15 is controlled by an X-ray control unit 16, and the X-ray control unit 16 is connected to a personal computer 20 in which a control software for controlling the entire X-ray CT apparatus is installed. The X-ray detector 12 is a combination of an image intensifier (I.I.) and a CCD camera, or alternatively, a flat panel detector (FPD), and is connected to the personal computer 20 via a CT image reconstruction arithmetic unit 18. In order to enlarge or reduce a fluoroscopic imaging region, the X-ray detector 12 is configured to approach and separate from the rotating stage 13, and the rotating stage 13 is also configured to approach or separate from the X-ray irradiation unit 11.

The rotating stage 13 is movable in the horizontal direction parallel to the optical axis of the X-ray that runs from the X-ray irradiation unit 11 to the X-ray detector 12 and in the vertical direction orthogonal to the optical axis of the X-ray. The stage driving mechanism 14 is connected to the personal computer 20 via a stage controller 17.

When performing X-ray CT imaging in a bending test, a test piece is attached to the bending tester 50 set on the rotating stage 13, and a bending load is applied to the test piece. The X-ray irradiation unit 11 emits an X-ray to the test piece. The rotating stage 13 is rotated about a rotation axis 100 orthogonal to the optical axis of the X-ray that runs from the X-ray irradiation unit 11 to the X-ray detector 12. In this state, the X-ray detector 12 detects X-rays that have passed through the test piece along all directions of 360 degrees around the test piece, and the data of passed-through X-rays is taken into the CT image reconstruction arithmetic unit 18.

The CT image reconstruction arithmetic unit 18 is a computer including a ROM, a RAM, a hard disk, or the like as a storage device which stores a program, data of detection performed by the X-ray detector 12, and the like, and a CPU as an arithmetic device. The CT image reconstruction arithmetic unit 18 constructs tomographic images (CT images) of a plurality of cross sections of the test piece using the taken-in data of X-rays that have passed through the test piece along all directions of 360 degrees. The CT images are transmitted from the CT image reconstruction arithmetic unit 18 to the personal computer 20, and are used for three-dimensional imaging by a three-dimensional image construction program installed in the personal computer 20.

A display unit 23 such as a liquid crystal display, and an operation unit 22 including a keyboard and a mouse are connected to the personal computer 20. The display unit 23 displays the CT images transmitted from the CT image reconstruction arithmetic unit 18 to the personal computer 20, and displays a three-dimensional image constructed using the CT images. Note that, the function of the CT image reconstruction arithmetic unit 18 may be integrated with the personal computer 20 and realized by a single computer as a peripheral device or software of the computer.

Figure 3:
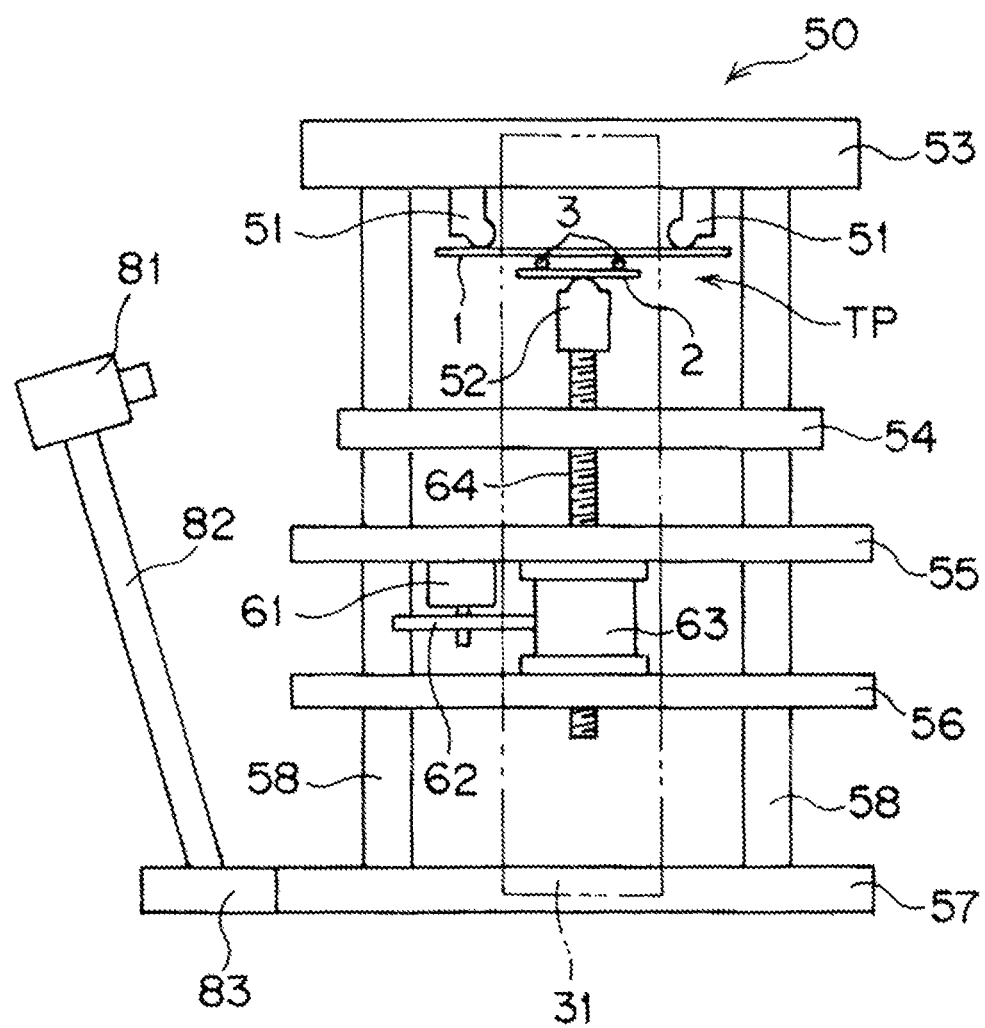
FIG. 3 is a front view of a bending tester 50.
Figure 4:
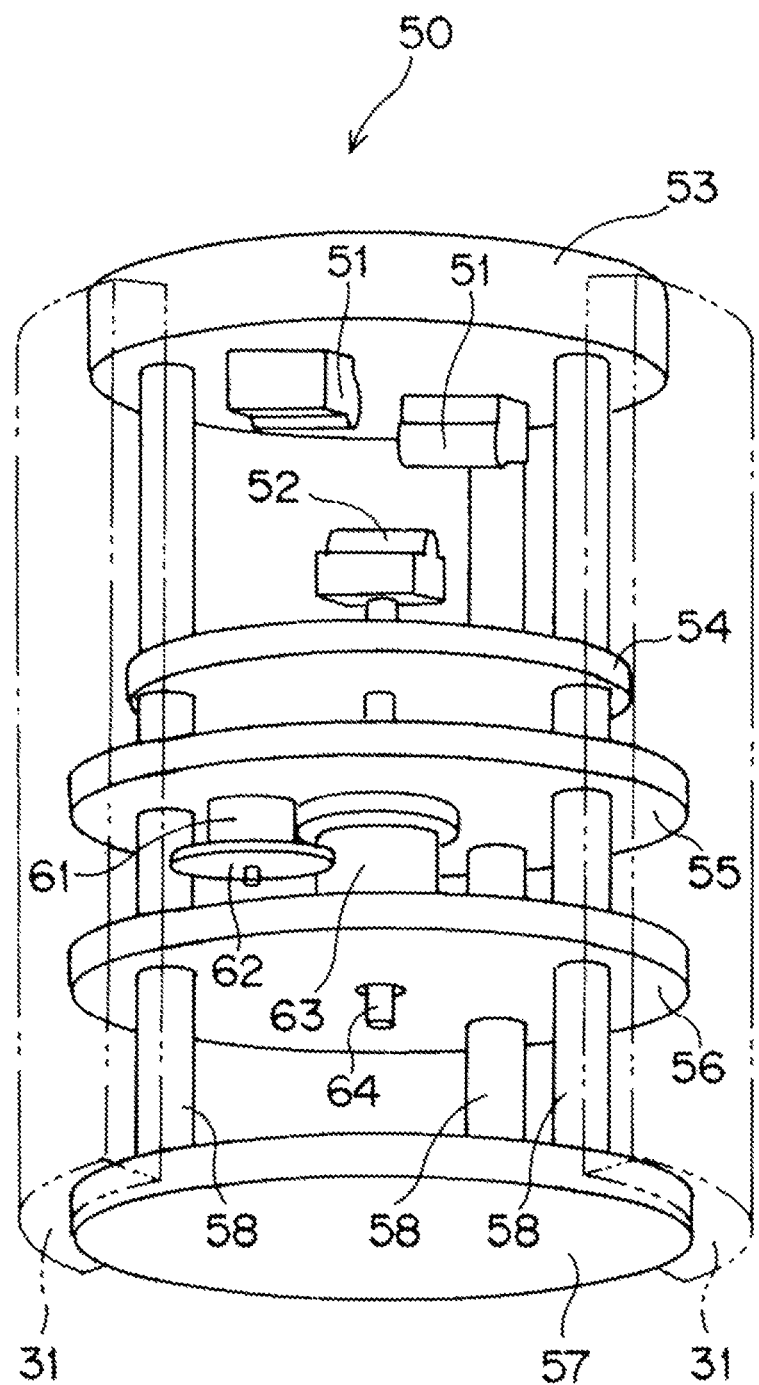
FIG. 4 is a perspective view of the bending tester 50.

Next, a configuration of the bending tester 50 as a load mechanism according to the present invention will be described. FIG. 3 is a front view of the bending tester 50. FIG. 4 is a perspective view of the bending tester 50. In FIG. 4, illustration of a camera 81 and connection members 82 and 83 is omitted.

The bending tester 50 performs a three-point bending test on a test piece TP using an indenter 52 and a pair of fulcrums 51. In this embodiment, the test piece TP is a printed circuit board, and includes a board 1 and an electronic component 2 joined to the board 1 by solder joints 3.

The bending tester 50 includes a base plate 57, three supports 58 erecting at even intervals on the base plate 57, a head plate 53, a pair of fixed plates 55 and 56, being fixed to the supports 58 at predetermined gaps, and a movable plate 54 which has through holes in which the supports 58 penetrate and is movable along the supports 58. The base plate 57, the head plate 53, and a pair of fixed plates 55 and 56 are connected to a pair of support members 31 described later.

A gear 63 rotatable between spacers provided to a pair of fixed plates 55 and 56 is disposed between the fixed plates 55 and 56. A nut screwed on a threaded rod 64 is disposed inside the gear 63. The threaded rod 64 is coupled to the movable plate 54, and the indenter 52 is disposed at the distal end of the threaded rod 64. A motor 61 is disposed on the lower surface of the fixed plate 55. A spur gear 62 meshing with the gear 63 is disposed on a rotation shaft of the motor 61. The motor 61 drives the spur gear 62 and the gear 63 to rotate, and thereby the threaded rod 64 screwed through the nut in the gear 63 moves upward or downward. As the threaded rod 64 moves upward or downward, the movable plate 54 and the indenter 52 move upward or downward. A pair of fulcrums 51 is disposed on the lower surface of the head plate 53. The test piece TP is sandwiched between a pair of fulcrums 51 and the indenter 52, and test force is applied by the indenter 52 along with the upward or downward movement of the indenter 52.

The connection member 83 is attached to a side of the base plate 57, and the connection member 82 which supports the camera 81 is fixed to the connection member 83. The camera 81 is for taking a picture of the test piece TP which is subjected to the bending test and X-ray CT imaging.

The supports 58 need to be made of a material having high rigidity to prevent deformation of the bending tester 50 caused by applying test force to the test piece TP. To prevent an artifact, the supports 58 need to be made of a material having high X-ray transmittance. These requirements can be achieved by using aluminum or CFRP for the supports 58. Furthermore, a pair of fulcrums 51 and the indenter 52 are also made of CFRP or the like to prevent an artifact.

The drive mechanism including the motor 61 and the gear 63 having a relatively large weight is disposed in a lower portion of the bending tester 50 to keep the center of gravity of the entire device low, so that the device can be stably set on the rotating stage 13.

Figure 5:
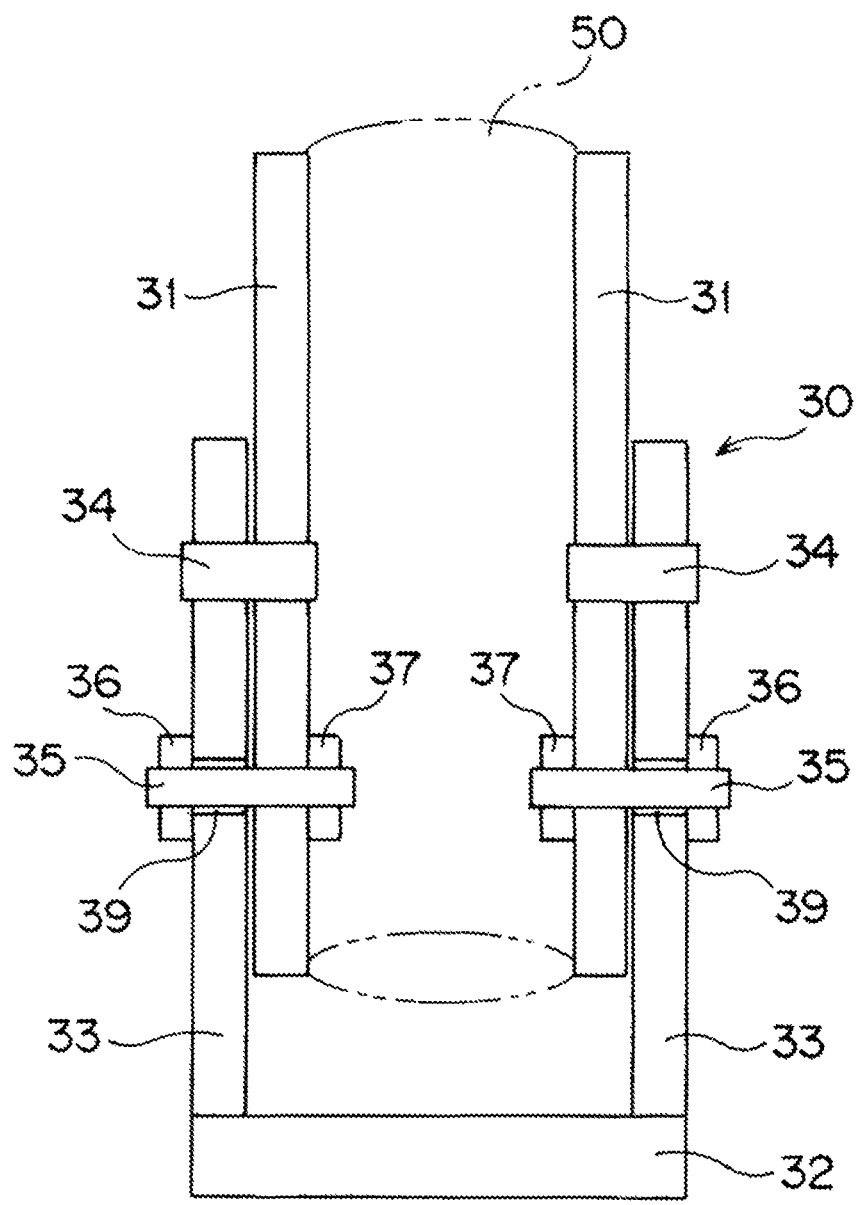
FIG. 5 is a front view of an angle changing mechanism 30.
Figure 6:
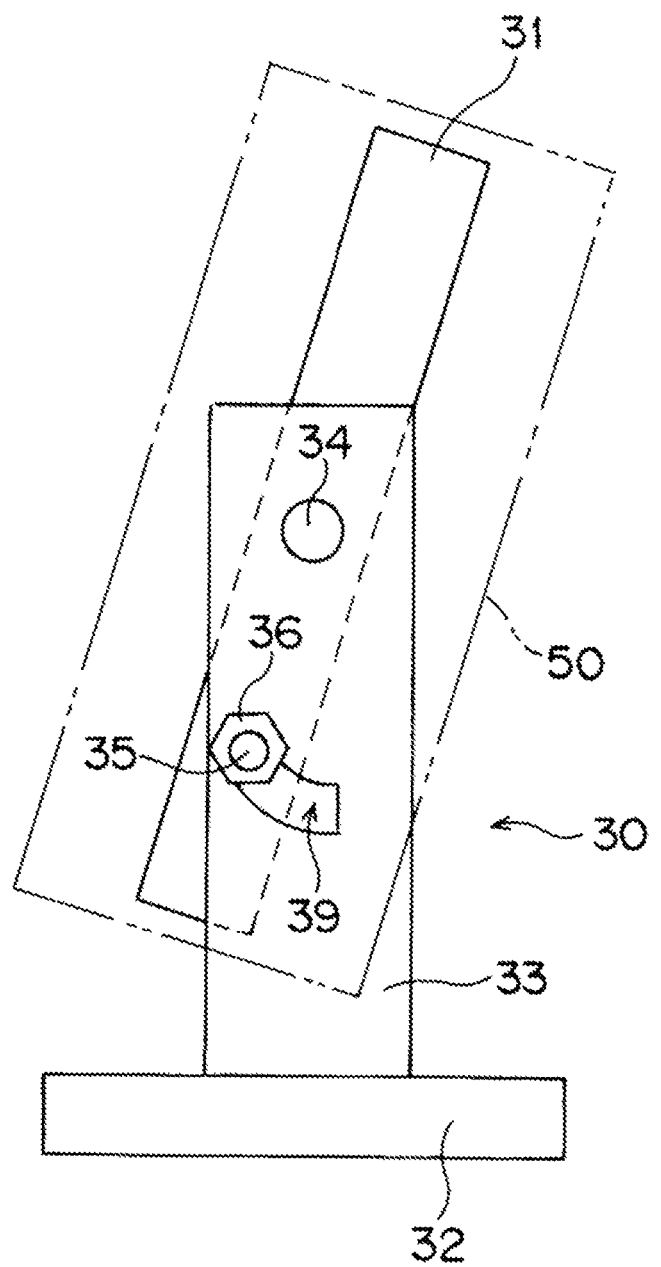
FIG. 6 is a side view of the angle changing mechanism 30.
Figure 7:
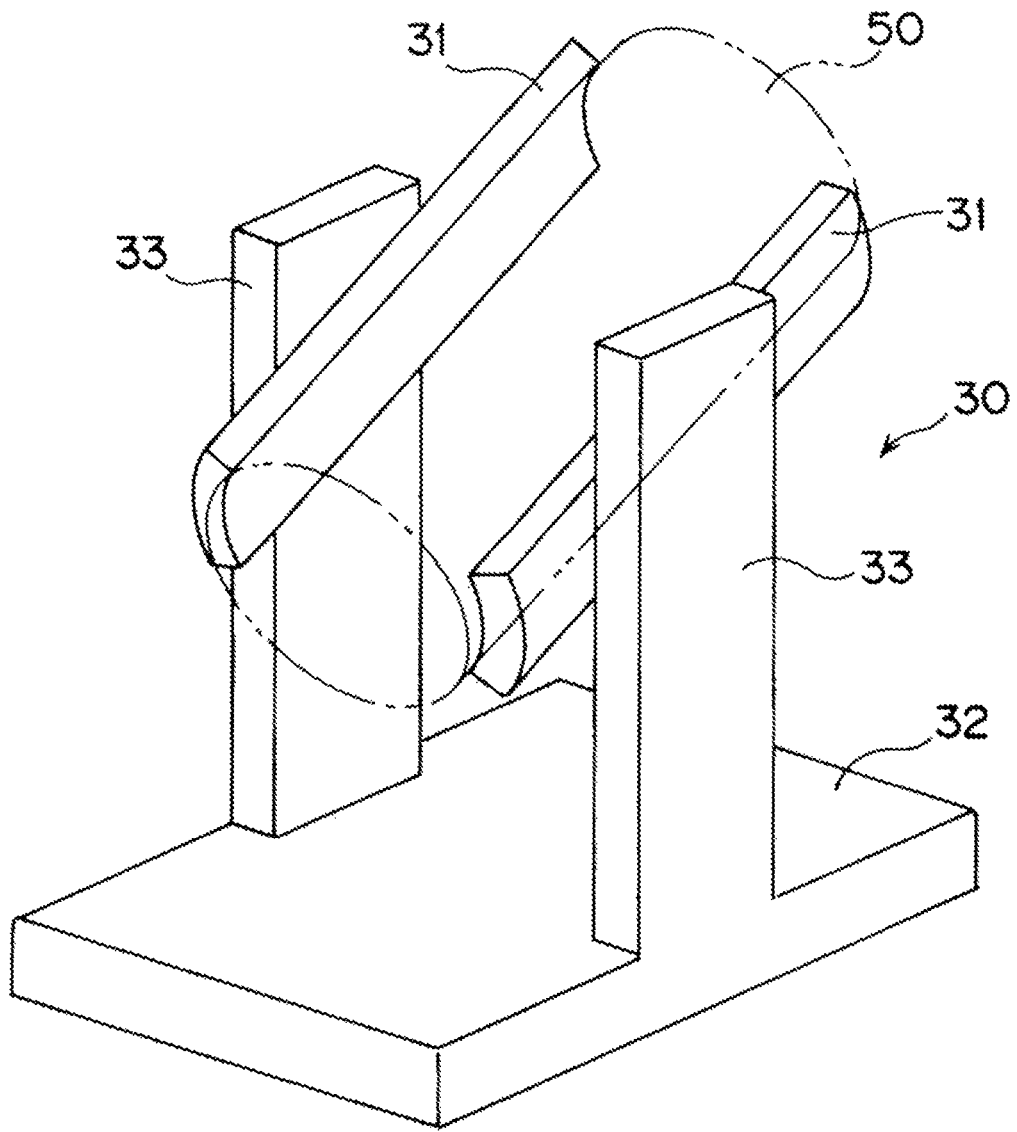
FIG. 7 is a perspective view of the angle changing mechanism 30.

Next, the configuration of the angle changing mechanism 30 which changes the tilt angle of the bending tester 50 as the load mechanism to change the angle between the direction of the test force applied to the test piece TP and the optical axis of the X-ray that runs from the X-ray irradiation unit 11 to the X-ray detector 12 will be described. FIG. 5 is a front view of the angle changing mechanism 30. FIG. 6 is a side view of the angle changing mechanism 30. FIG. 7 is a perspective view of the angle changing mechanism 30. In these drawings, the bending tester 50 is schematically shown by imaginary lines. In FIG. 7, illustration of support shafts 34, bolts 35, nuts 36, and holes 39 is omitted.

A pair of support members 31 coupled to the base plate 57, the head plate 53, and a pair of fixed plates 55 and 56 to support the bending tester 50 is coupled, via support shafts 34, to a pair of standing members 33 erecting on the base 32, and the bending tester 50 swings about the support shafts 34 together with the pair of support members 31. An arc-shaped hole 39 is formed in each of the standing members 33. The bolt 35 penetrating the hole 39 is provided in each support member 31, and the nut 36 and a nut 37 are disposed at both ends of the bolt 35. When the nuts 36 are loosened, the bending tester 50 is swingable about the support shafts 34, and when the nuts 36 are tightened, swinging of the bending tester 50 is restricted. The tilt angle of the bending tester 50 can be changed by the action of the angle changing mechanism 30, whereby the angle between the direction of the test force applied to the test piece TP by the bending tester 50 and the optical axis of the X-ray can be changed.

Figure 8:
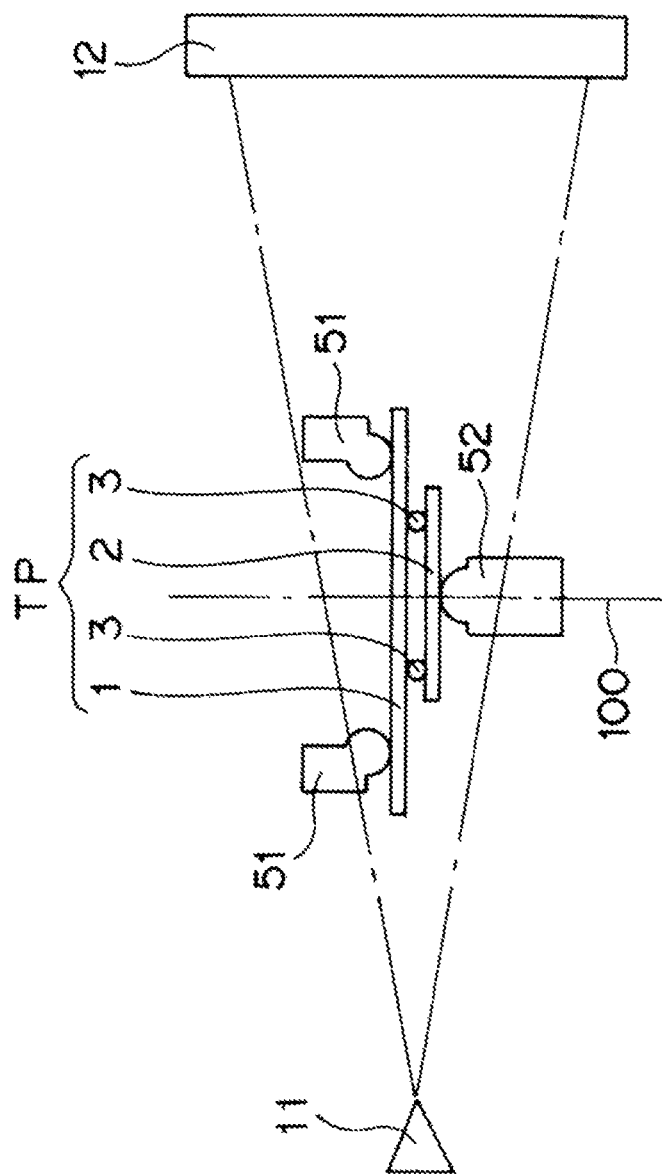
FIG. 8 is a schematic view illustrating X-ray CT imaging performed with test force applied to a test piece TP.
Figure 9:
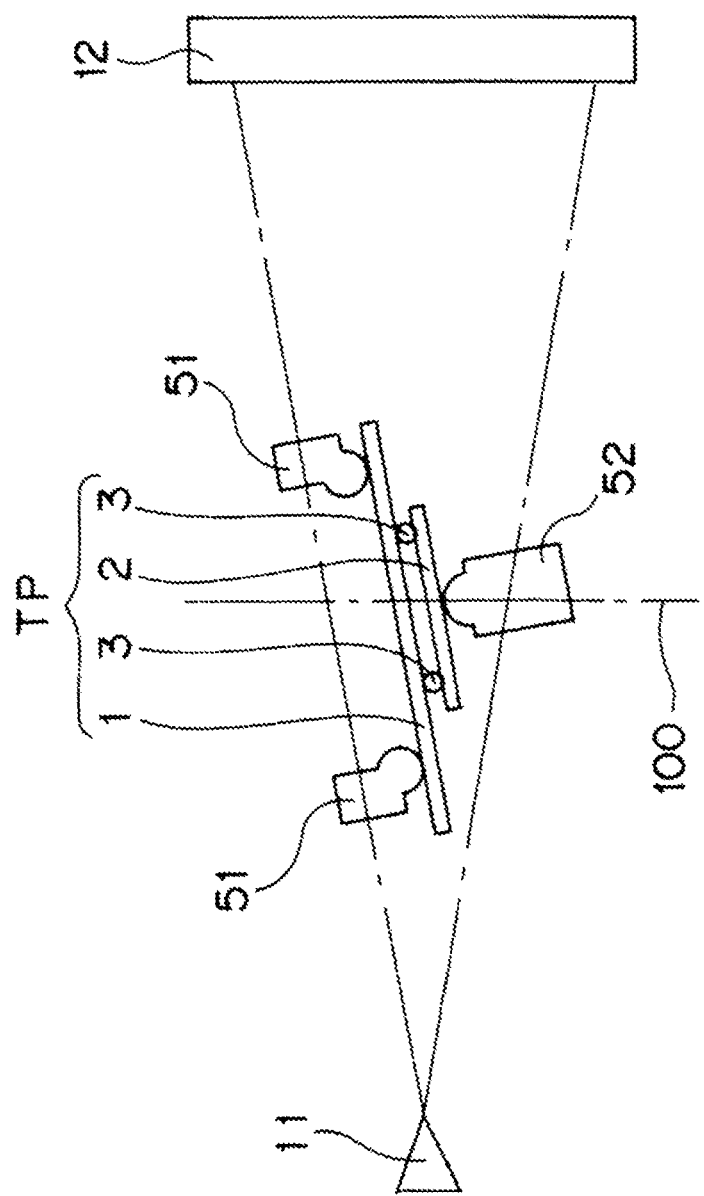
FIG. 9 is a schematic view illustrating X-ray CT imaging performed with test force applied to the test piece TP.
Figure 10:
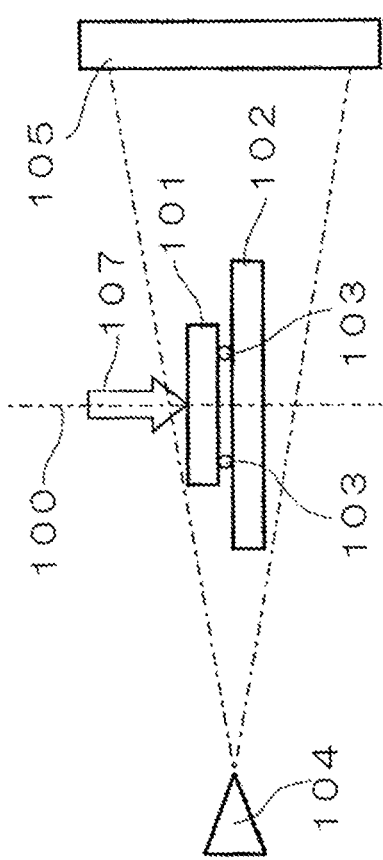
FIG. 10 is a schematic view illustrating a bending test performed on a printed circuit board as a test piece.

An operation of performing X-ray CT imaging with test force applied to the test piece TP by the bending tester 50 in the X-ray CT imaging apparatus configured as described above will be described. FIGS. 8 and 9 are schematic diagrams illustrating X-ray CT imaging performed with test force applied to the test piece TP.

When performing X-ray CT imaging with test force applied to the test piece TP by the bending tester 50, the test piece TP is sandwiched between a pair of fulcrums 51 and the indenter 52 as illustrated in FIGS. 8 and 9. Bending test force is applied to the test piece TP by moving the indenter 52 toward the pair of fulcrums 51 by driving the motor 61 illustrated in FIGS. 3 and 4. In this state, by rotating the rotating stage 13, the bending tester 50 rotates together with the test piece about the rotation axis 100 along the vertical direction. In this state, the X-ray irradiation unit 11 emits an X-ray, and the X-ray detector 12 detects the X-ray that has passed through the test piece TP, thereby performing X-ray CT imaging. In parallel with the X-ray CT imaging, the camera 81 takes a picture of the bending region of the test piece TP.

The test piece TP is a printed circuit board, and includes the board 1 and the electronic component 2 joined to the board 1 by the solder joints 3. The solder joints 3 are typically disposed on the same plane on the board 1. Thus, as illustrated in FIG. 8, when the X-ray CT imaging is performed with the board 1 of the test piece TP disposed in a horizontal direction, a plurality of solder joints 3 of the test piece TP revolves in the same plane. This causes a noticeable artifact due to the metal contained in the solder joints 3 in an image captured by the X-ray detector 12. Occurrence of such a noticeable artifact makes it difficult to accurately observe the observation target region of the test piece TP including the solder joints 3.

Thus, in the X-ray CT apparatus according to the embodiment, as illustrated in FIG. 9, the tilt angle of the bending tester 50 is changed by the action of the angle changing mechanism 30 to change the angle between the direction of the test force applied to the test piece TP by the bending tester 50 and the optical axis of the X-ray. The tilt angle of the bending tester 50 is set to such an angle that allows as few as possible among a plurality of solder joints 3 to be disposed in the course of the X-ray that is emitted from the X-ray irradiation unit 11, passes through the test piece TP, and reaches the X-ray detector 12. This enables to suppress the occurrence of an artifact due to the metal contained in the solder joints 3 in the image captured by the X-ray detector 12.

The camera 81 is connected to the base plate 57 of the bending tester 50 via the connection members 82 and 83. Thus, even when the tilt angle of the bending tester 50 is changed, a picture of the bending region of the test piece TP can be continuously taken by the camera 81.

In the embodiment illustrated in FIGS. 8 and 9, the test piece TP including the board 1 and the electronic component 2 joined to the board 1 by the two solder joints 3 is schematically illustrated. An actual printed circuit board, however, may have a number of solder joints, and those solder joints are typically arranged substantially on the same plane. As in the above-described embodiment, tilting the test piece TP together with the bending tester 50 suppress the solder joints being disposed in the same plane, and can thereby suppress the occurrence of an artifact. This enables to obtain a high-quality X-ray CT image.

In the embodiment described above, the printed circuit board including the board 1 and the electronic component 2 joined to the board 1 by the solder joints 3 is used as the test piece TP. However, a test piece of CFRP or GFRP may be used. Even in such a case, tilting the test piece to reduce the distance by which the X-ray passes through the test piece suppresses the occurrence of an artifact, and thereby a high-quality X-ray CT image can be obtained.

In the embodiment described above, a three-point bending test using the indenter 52 and a pair of fulcrums 51 is performed. However, the present invention may be applied to a case where a four-point bending test using a pair of indenters is performed. Furthermore, the test is not limited to a bending test, but may be a different kind of material test in which test force is applied to the test piece TP, such as a tensile test.

Furthermore, in the above-described embodiment, the bending tester 50 is rotated by the rotating stage 13 disposed between the X-ray irradiation unit 11 and the X-ray detector 12. However, the bending tester 50 may be disposed on a fixed stage, and the X-ray irradiation unit 11 and the X-ray detector 12 may synchronously revolve along the outer circumference of the bending tester 50.

It is understood by those skilled in the art that the exemplary embodiments described above are specific examples of the following aspects.

(Clause 1)

An X-ray CT apparatus including
an X-ray imaging system including an X-ray irradiation unit and an X-ray detector,
a stage disposed between the X-ray irradiation unit and the X-ray detector,
a rotation mechanism configured to relatively rotate the X-ray imaging system and the stage about a rotation axis orthogonal to an optical axis of an X-ray that runs from the X-ray irradiation unit to the X-ray detector, and
a load mechanism which is set on the stage and is configured to apply test force to a test piece,
the X-ray CT apparatus including
an angle changing mechanism configured to tilt the load mechanism to change the direction of the test force applied to the test piece by the load mechanism from a direction orthogonal to the optical axis of the X-ray.

With the X-ray CT apparatus according to clause 1, a load mechanism is tilted to change the direction of the test force applied to the test piece by the load mechanism from a direction orthogonal to the optical axis of the X-ray, and thereby occurrence of an artifact is suppressed and a high-quality X-ray CT image can be obtained.

(Clause 2)

The X-ray CT apparatus according to clause 1, where the angle changing mechanism is configured to change a tilt angle of the load mechanism to change an angle between the direction of the test force applied to the test piece and the optical axis of the X-ray.

With the X-ray CT apparatus according to clause 2, by adjusting the angle between the direction of the test force applied to the test piece and the optical axis of the X-ray to an angle in which occurrence of an artifact is minimum, an X-ray CT image with higher image quality can be obtained.

(Clause 3)

The X-ray CT apparatus according to clause 1 or 2, where the load mechanism includes a pair of fulcrums which comes into contact with the test piece, an indenter which comes into contact with the test piece from a direction opposite to a direction in which the pair of fulcrums comes into contact with the test piece, and a test force applying mechanism configured to change a distance between the pair of fulcrums and the indenter, and performs a bending test on the test piece.

With the X-ray CT apparatus according to clause 3, X-ray CT imaging can be performed while a three-point bending test is being performed.

(Clause 4)

The X-ray CT apparatus according to any one of clauses 1 to 3, further including a camera configured to take a picture of the test piece, and a connection member connecting the load mechanism to the camera so that the camera tilts together with the load mechanism.

With the X-ray CT apparatus according to clause 4, a picture of the test piece can be taken by the camera regardless of the tilt angle of the load mechanism.

Note that, the above description is for explaining the embodiments of the present invention, and is not by means of limiting the scope of the present invention.

The invention claimed is:

1. An X-ray CT apparatus including an X-ray imaging system including an X-ray irradiation unit and an X-ray detector, a stage disposed between the X-ray irradiation unit and the X-ray detector, a rotation mechanism configured to relatively rotate the X-ray imaging system and the stage about a rotation axis orthogonal to an optical axis of an X-ray that runs from the X-ray irradiation unit to the X-ray detector, and a load mechanism which is set on the stage and is configured to apply test force to a test piece, the X-ray CT apparatus comprising:

an angle changing mechanism configured to tilt the load mechanism to change a direction of the test force applied to the test piece by the load mechanism from a direction orthogonal to the optical axis of the X-ray;

a camera configured to take a picture of the test piece; and a connection member connecting the load mechanism to the camera so that the camera tilts together with the load mechanism.

2. The X-ray CT apparatus according to claim 1, wherein the angle changing mechanism is configured to change a tilt angle of the load mechanism to change an angle between the direction of the test force applied to the test piece and the optical axis of the X-ray.

3. The X-ray CT apparatus according to claim 1, wherein the load mechanism includes a pair of fulcrums which comes into contact with the test piece, an indenter which comes into contact with the test piece from a direction opposite to a direction in which the pair of fulcrums comes into contact with the test piece, and a test force applying mechanism configured to change a distance between the pair of fulcrums and the indenter, and performs a bending test on the test piece.

\* \* \* \* \*